(12) United States Patent
Odim

(10) Patent No.: US 12,194,183 B2
(45) Date of Patent: Jan. 14, 2025

(54) VACUUM-RELEASING STERILANT POD

(71) Applicant: American Sterilizer Company, Mentor, OH (US)

(72) Inventor: Isaac Odim, Minneapolis, MN (US)

(73) Assignee: American Sterilizer Company, Mentor, OH (US)

(*) Notice: Subject to any disclaimer, the term of this patent is extended or adjusted under 35 U.S.C. 154(b) by 678 days.

(21) Appl. No.: 17/292,574

(22) PCT Filed: Nov. 7, 2019

(86) PCT No.: PCT/US2019/060196
§ 371 (c)(1),
(2) Date: May 10, 2021

(87) PCT Pub. No.: WO2020/106460
PCT Pub. Date: May 28, 2020

(65) Prior Publication Data
US 2021/0393830 A1    Dec. 23, 2021

Related U.S. Application Data

(60) Provisional application No. 62/769,114, filed on Nov. 19, 2018.

(51) Int. Cl.
| | | |
|---|---|---|
| A61L 2/20 | (2006.01) | |
| A61L 2/26 | (2006.01) | |
| A61L 101/02 | (2006.01) | |
| A61L 101/36 | (2006.01) | |

(52) U.S. Cl.
CPC .......... *A61L 2/208* (2013.01); *A61L 2/26* (2013.01); *A61L 2101/02* (2020.08); *A61L 2101/36* (2020.08); *A61L 2202/122* (2013.01)

(58) Field of Classification Search
CPC ....... A61L 2/208; A61L 2/26; A61L 2202/122
See application file for complete search history.

(56) References Cited

U.S. PATENT DOCUMENTS

| | | |
|---|---|---|
| 4,400,357 A | 8/1983 | Hohmann |
| 4,817,800 A | 4/1989 | Williams et al. |
| 4,872,556 A | 10/1989 | Farmer |

(Continued)

FOREIGN PATENT DOCUMENTS

| | | |
|---|---|---|
| CN | 104397899 | 3/2015 |
| CN | 204337340 U | 5/2015 |

OTHER PUBLICATIONS

International Preliminary Report on Patentability mailed Jun. 3, 2021, of International PCT Application No. PCT/US19/60196 filed Nov. 7, 2019.

(Continued)

*Primary Examiner* — Sean E Conley

(57) ABSTRACT

A decontamination system for a lumen device is depicted. The decontamination system, in some embodiments, includes a lumen device container, a pump, and a sealed container with decontamination fluid. The lumen device container defines a lumen device receiving area. The pump is configured to reduce pressure within the lumen device receiving area. The sealed container is configured to release the decontamination fluid into the lumen device receiving area responsive to a pressure drop applied to the sealed container.

20 Claims, 2 Drawing Sheets

(56) References Cited

U.S. PATENT DOCUMENTS

| | | | |
|---|---|---|---|
| 4,909,287 | A | 3/1990 | Williams et al. |
| 4,943,414 | A | 7/1990 | Jacobs et al. |
| 5,641,455 | A | 6/1997 | Rosenlund et al. |
| 5,700,245 | A | 12/1997 | Sancoff et al. |
| 6,113,851 | A | 9/2000 | Soloshenko et al. |
| 7,179,419 | B2 | 2/2007 | Lin et al. |
| 8,641,981 | B2 | 2/2014 | Heckenberger et al. |
| 9,044,748 | B2 | 6/2015 | Koyama |
| 9,114,971 | B2 | 8/2015 | Rasmussen et al. |
| 10,279,060 | B2 | 5/2019 | Deprey et al. |
| 2003/0206827 | A1* | 11/2003 | Lin ................ A61L 2/208 422/33 |
| 2011/0176959 | A1 | 7/2011 | Ko |
| 2012/0043352 | A1* | 2/2012 | Rasmussen ...... B67D 1/0412 222/105 |

OTHER PUBLICATIONS

International Search Report and Written Opinion of the International Searching Authority Dated Feb. 4, 2020, of International PCT Application No. PCT/US2019/060196 filed Nov. 7, 2019.

Peer Contribution by China National Intellectual Property Jan. 20, 2020, of International PCT Application No. PCT/US2019/060196 filed Nov. 7, 2019.

Peer Contribution by European Patent Office Jan. 13, 2020, of International PCT Application No. PCT/US2019/060196 filed Nov. 7, 2019.

Peer Contribution by Japan Patent Office Jan. 17, 2020, of International PCT Application No. PCT/US2019/060196 filed Nov. 7, 2019.

Peer Contribution by Korean Intellectual Property Office Jan. 20, 2020, of International PCT Application No. PCT/US2019/060196 filed Nov. 7, 2019.

* cited by examiner

VACUUM-RELEASING STERILANT POD

PRIORITY CLAIM

This application claims priority to and the benefit of U.S. Provisional application with Ser. No. 62/769,114, filed on Nov. 19, 2018, entitled VACUUM-RELEASING STERILANT POD, which is herein incorporated by reference in its entirety.

TECHNICAL FIELD

This disclosure relates generally to decontamination of medical devices; in particular, this disclosure relates to a decontamination system with pods that dispense decontamination fluid during a pressure change in a decontamination cycle.

BACKGROUND

Robust medical instruments are often sterilized at high temperatures. Commonly, the instruments are sterilized in a steam autoclave under a combination of high temperature and pressure. While such sterilization methods are very effective for more durable medical instruments, advanced medical instruments formed of rubber and plastic components with adhesives are delicate and wholly unsuited to the high temperatures and pressures associated with a conventional steam autoclave. Steam autoclaves have also been modified to operate under low pressure cycling programs to increase the rate of steam penetration into the medical devices or associated packages of medical devices undergoing sterilization. Steam sterilization using gravity, high pressure or pre-vacuum create an environment where rapid changes in temperature can take place. In particular, highly complex instruments which are often formed and assembled with very precise dimensions, close assembly tolerances, and sensitive optical components, such as endoscopes, may be destroyed or have their useful lives severely curtailed by harsh sterilization methods employing high temperatures and high or low pressures.

Endoscopes can also present problems in that such devices typically have numerous exterior crevices and interior lumens which can harbor microbes. Microbes can be found on surfaces in such crevices and interior lumens as well as on exterior surfaces of the endoscope. Other medical or dental instruments which comprise lumens, crevices, and the like can also provide challenges for decontaminating various internal and external surfaces that can harbor microbes.

Existing decontamination systems introduce decontamination fluid to the endoscope using an injection system. However, these injection systems add complexity to the decontamination system by requiring nozzles, fluid monitoring systems and other components. Also, these injection systems increase the cost of decontamination systems.

Therefore, a need exists that overcomes one or more of the disadvantages of present decontamination systems.

SUMMARY OF THE INVENTION

According to one aspect, this disclosure provides a decontamination system for a lumen device. In some embodiments, the decontamination system comprises a lumen device container, a pump, and a sealed container with decontamination fluid. The lumen device container defines a lumen device receiving area. The pump is configured to reduce pressure within the lumen device receiving area. The sealed container is configured to release the decontamination fluid into the lumen device receiving area responsive to a pressure drop applied to the sealed container.

According to another aspect, this disclosure provides a sterilant pod for a lumen decontamination system. The sterilant pod comprises a sealed container defining a cavity in which a decontamination fluid is stored. The sealed container is configured to release the decontamination fluid responsive to a predetermined pressure drop proximate the sealed container.

According to a further aspect, this disclosure provides a method of decontaminating a lumen device. The method includes the step of providing a lumen decontamination system with a lumen device receiving area. A sealed container with decontamination fluid is placed into the lumen device receiving area. The decontamination fluid is released from the sealed container by generating a pressure drop in the lumen device receiving area.

BRIEF DESCRIPTION OF THE DRAWINGS

The present disclosure will be described hereafter with reference to the attached drawings which are given as non-limiting examples only, in which.

Figure 1:
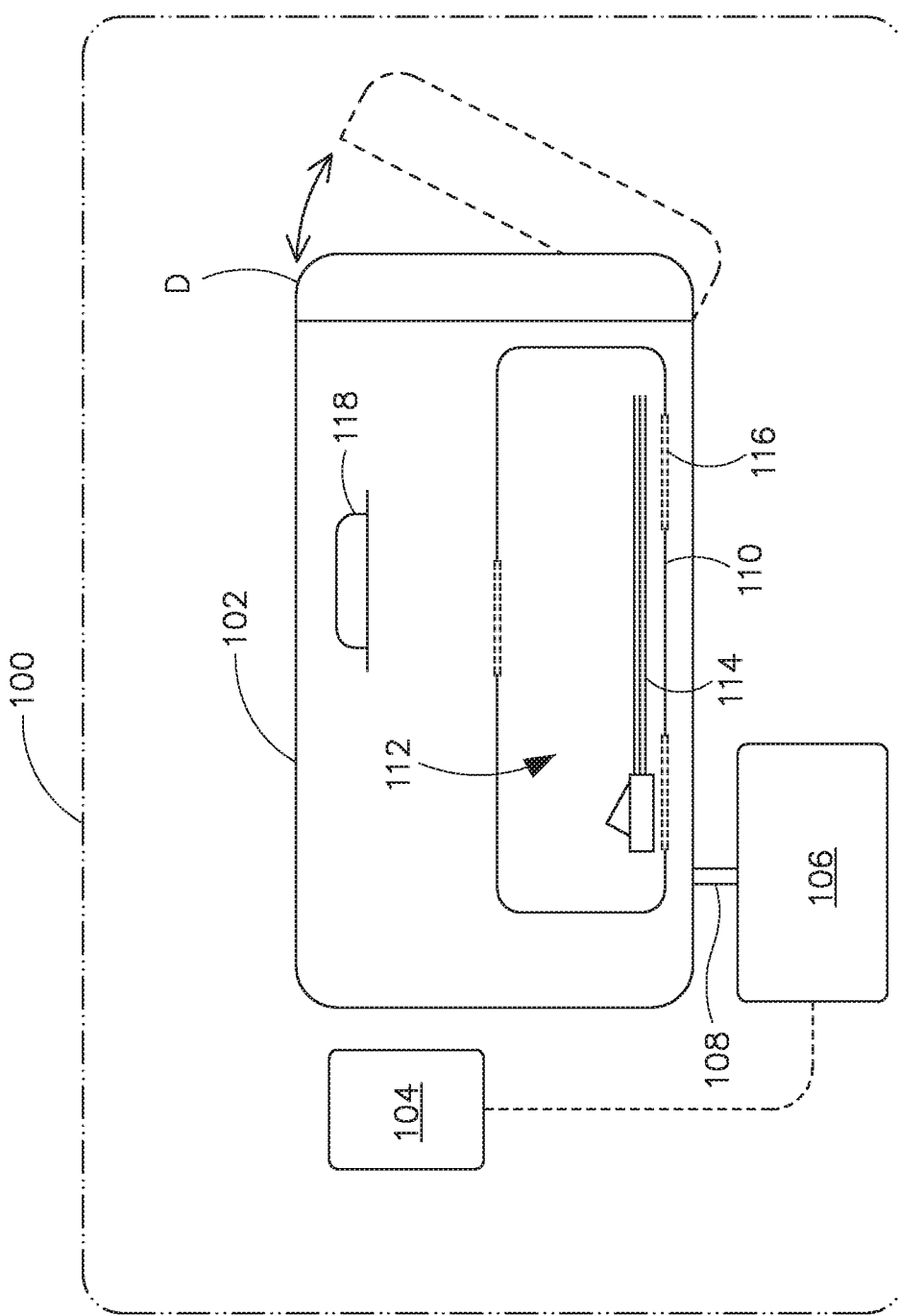
FIG. 1 is diagrammatic view of a system for decontaminating a medical device according to an embodiment of the present disclosure.

Corresponding reference characters indicate corresponding parts throughout the several views. The components in the figures are not necessarily to scale, emphasis instead being placed upon illustrating the principals of the invention. The exemplification set out herein illustrates embodiments of the invention, and such exemplification is not to be construed as limiting the scope of the invention in any manner.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

This disclosure relates to delivery of decontamination fluid in a decontamination system. In some embodiments, this system uses a sealed container or pod filled with a decontamination fluid. At ambient pressure, the decontamination fluid is contained within the pod. During a pressure drop in a decontamination cycle, the pressure difference between the inside and outside of the pod causes decontamination fluid to be released. For example, the pressure drop could cause a seal on the pod to burst, thereby releasing the decontamination fluid within the pod. In another embodiment, the pod may incorporate a one-way valve that is configured to open upon a predetermined pressure drop, thereby releasing decontamination fluid through the valve.

FIG. 1 is a diagrammatic view of one embodiment of a system 100 for decontaminating a medical, dental, or other device having one or more lumens extending there-through. In the example shown, the system 100 includes a decontamination chamber 102, a system controller 104, and a pressure control system 106, such as a vacuum pump, in fluid communication with the decontamination chamber 102 via a conduit 108. A lumen device container 110 defining a lumen receiving area 112 to receive a lumen device 114 for decontamination may be placed within the decontamination chamber 102. In the illustrated embodiment, the container 110 includes a plurality of openings or pores 116. In the embodiment shown, a sealed container or pod 118 filled with decontamination fluid 120 (FIGS. 2 and 4) may be placed within the decontamination chamber 102. In some cases, the sterilant pod 118 may be attached, connected with or fixedly received within the decontamination chamber 102, such as with a frictional or interference fit with the interior of the decontamination chamber 102. The sterilant pod 118 is arranged within the decontamination chamber 102 to introduce decontamination fluid 120 to the lumen device 114 during one or more decontamination cycles of the system 100. Although a single sterilant pod 118 is shown for purposes of example, more than one sterilant pod 118 could be used depending on the circumstances.

The system controller 104 provides control signals to and/or receives condition sensing and equipment status signals from the decontamination chamber 102 and/or pressure control system 106. The delivery of the decontamination fluid 120 within the sterilant pod 118 can be controlled by the system controller 104 by selectively introducing pressure change(s) in the decontamination chamber 102 with the pressure control system 106. In some embodiments, the system 100 can be assembled in a device small enough to sit on a tabletop or counter. For example, the decontamination chamber 102 may have an interior volume of less than about ten cubic feet. The lumen device 114 to be decontaminated can be placed into the decontamination chamber 102 by opening the door D and placing the lumen device 114 on a rack or other supporting assembly in the interior of the decontamination chamber 102. In some embodiments, the lumen device 114 may be enclosed in the container 110 before being placed in the decontamination chamber 102.

Figure 2:
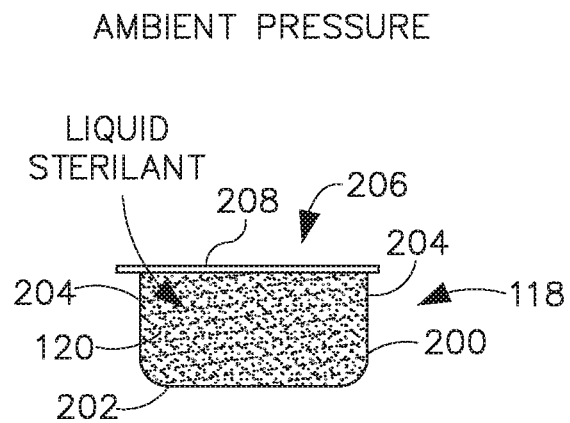
FIG. 2 is a side cross-sectional view of an example sterilant pod under ambient pressure according to an embodiment of the present disclosure.
Figure 4:
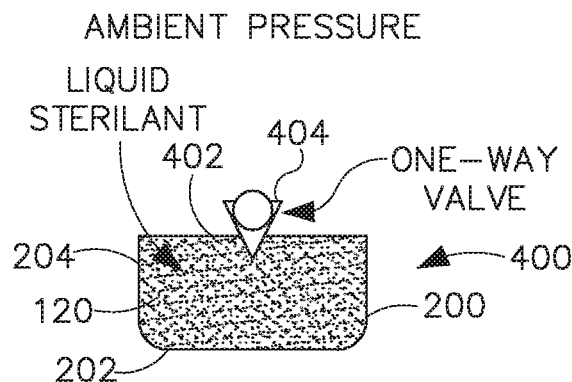
FIG. 4 is a side cross-sectional view of an example sterilant pod under ambient pressure according to another embodiment of the present disclosure.

The sterilant pod 118 is configured to hold a decontamination fluid 120 (FIGS. 2 and 4). In some embodiments, the decontamination fluid 120 can be a chemical or other substance suitable for use in a sterilization process that complies with the International Organization for Standardization (ISO) standard ISO/TC 198, Sterilization of Healthcare Products and/or the Association for the Advancement of Medical Instrumentation (AAMI) standard ANSI/AAMI/ISO 11140-1:2005, "Sterilization of Healthcare Products-Chemical Indicators-Part I: General Requirements" (Arlington, Va.: AAMI 2005). In some embodiments, the decontamination fluid 120 can be a room temperature (e.g., 20° C. to 25° C.) substance that can be dispersed as a fluid, such as a liquid, a vapor, or a combination thereof (such as a fog) during the decontamination process. Suitable substances for the decontamination fluid 120 include but are not limited to hydrogen peroxide ($H_2O_2$) and/or peracetic acid (PAA). The decontamination fluid 120 may be released due to a pressure drop within the decontamination chamber 102 by the pressure control system 106.

The container 110 is sized so that the lumen device 114 to be decontaminated fits within the container 110. In some embodiments, the container 110 may be generally described as having a top, a bottom, and four sides extending between the top and bottom to create a cube-like structure. However, the container 110 may have any suitable shape which encloses the lumen device 114. In some embodiments, the container 110 may be formed from a rigid material such that the container 110 has a rigid or structured shape. Alternatively, the container 110 may be formed from a flexible material such that the container 110 has a flexible shape. In some embodiments, the container 110 may be a terminal package. Suitable materials for the container 110 include but are not limited to a polymeric non-woven sheet, such as spun-bonded polyethylene (e.g., Tyvek®, sold by E.I. du Pont de Nemours and Company, Wilmington, Del.), and polymeric materials such as polyester and polypropylene. Suitable materials for container 110 having a rigid or structured shape include but are not limited to various metals such as aluminum, stainless steel and/or various polymers in rigid form such as polyethylene and/or polypropylene.

The lumen device 114 may be positioned within the container 110 and subjected to one or more decontamination cycles. Suitable lumen devices include any medical, dental or other device having at least one lumen extending through at least a portion of the device. In some embodiments, the lumen device 114 may include at least one lumen extending the entire length of the device. For example, the lumen device 114 may be an endoscope.

The container 110 may be configured to prevent or reduce microbes and/or other contaminants from entering the container 110. In some embodiments, for example, the container 110 can include a material suitable for allowing flow of a decontamination fluid, such as hydrogen peroxide ($H_2O_2$) and/or peracetic acid (PAA), into the lumen receiving area 112 of the container 110 and blocking or reducing the flow of contaminants into the interior of the container 110. In the illustrated embodiment, the container 110 includes a plurality of openings or pores 116 for allowing flow of the decontamination fluid 120 into the container 110. In some embodiments, the pores 116 may be sized so as to allow the decontamination fluid 120 and/or air to communicate into and out of the container 110 as well as prevent microbes from entering the container 110.

To decontaminate a lumen device, such as a medical, dental or other device, the lumen device 114 may be sealed within the container 110 and placed in the decontamination chamber 102. The lumen device 114 is then subjected to a decontamination process which may include one or more decontamination cycles. A suitable cycle may include adjusting the pressure of the decontamination chamber 102 to a suitable range, such as to a pressure less than 10 Torr, and introducing the decontamination fluid 120 into the decontamination chamber 102 via the sterilant pod 118. The decontamination fluid 120 may be held within the decontamination chamber 102 for a period of time to facilitate the decontamination of the lumen device 110, and in particular, the exterior surfaces of the lumen device 114. The decontamination time could vary from a few seconds to several hours or longer depending on the sterilization process, the decontamination fluid being used, the vacuum pressures, the amount of decontamination fluid to be vaporized, and other factors. Similarly, the decontamination fluid 120 may be held within the lumen device 114 for a period of time to facilitate the decontamination of the interior surfaces or lumen(s) of the lumen device 114. When the decontamination fluid 120 has been held in the decontamination chamber 102 for the desired or programmed amount of time, the system controller 104 can vent the decontamination chamber 102 to a higher, but typically sub-atmospheric pressure. The system controller 104 can then hold the pressure within the decontamination chamber 102 for a period of time to further facilitate the decontamination of the load. Following the hold period, the system controller 104 may evacuate the decontamination chamber 102 to remove the decontamination fluid 120 residuals from the decontamination chamber 102, followed by venting the decontamination chamber 102. This cycle or steps may be repeated or extended as part of a comprehensive cycle.

Figure 3:
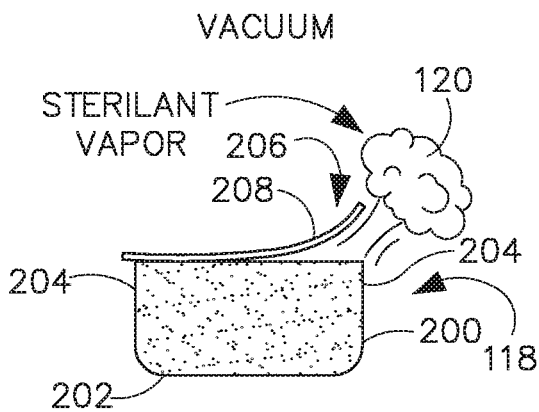
FIG. 3 is a side cross-sectional view of the example sterilant pod shown in FIG. 2 under a pressure drop to dispense decontamination fluid according to an embodiment of the present disclosure.

FIGS. 2 and 3 show an example sterilant pod 118 according to an embodiment of this disclosure. In the example shown, the sterilant pod 118 comprises a container 200 defining a cavity for holding the decontamination fluid 120. As shown, the container 200 includes a bottom wall 202, side walls 204 and an opening 206 covered by a seal 208. Although the example shown has a seal on top of the container 200, other walls of the container, such as the bottom and/or side wall(s), could be formed with a seal to dispense decontamination fluid. The container 200 could be formed from suitable materials for holding the decontamination fluid 120, such as various types of plastic and/or metals. The seal 208, which could be a membrane, is configured to break or burst in response to a predetermined pressure drop within the decontamination chamber 102, thereby releasing the decontamination fluid 120 within the container 200 out the opening 206.

At ambient pressure, which is shown in FIG. 2, the decontamination fluid 120 is contained within the sterilant pod 118. The seal 208 prevents decontamination fluid 120 from escaping the container 200 at ambient pressure. During a pressure drop in a decontamination cycle, which is shown in FIG. 3, the pressure difference between the inside and outside of the sterilant pod 118 causes the decontamination fluid 120 to be released. For example, the pressure drop could cause the seal 208 on the sterilant pod 118 to burst, thereby releasing the decontamination fluid 120 within the pod 118. The pressure at which the seal 208 of the sterilant pod 118 bursts could vary depending on the expected pressures within the decontamination chamber 102 during the decontamination cycles. In some embodiments, the seal 208 could burst when the pressure in the decontamination chamber 102 is less than 10 Torr.

Figure 5:
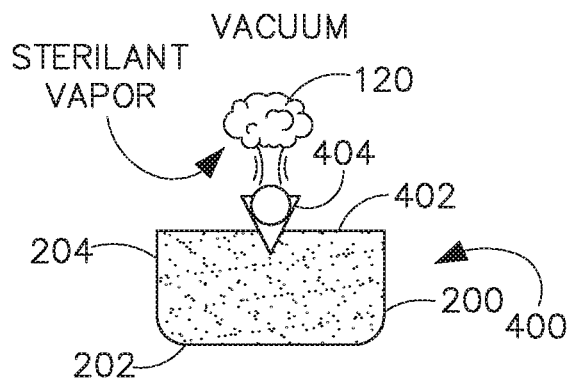
FIG. 5 is a side cross-sectional view of the example sterilant pod shown in FIG. 4 under a pressure drop to dispense decontamination fluid according to an embodiment of the present disclosure.

FIGS. 4 and 5 show a sterilant pod 400 according to another embodiment. In this embodiment, instead of releasing the decontamination fluid 120 by bursting the seal 208, a one-way valve dispenses decontamination fluid 120 based on pressure changes. As shown, the container 200 includes a top wall 402 with a one-way valve 404. However, even though the valve 404 is shown in the top wall 402 in this example, other walls of the container 200, such as the bottom and/or side wall(s), could be formed with a valve 404 to dispense decontamination fluid. The one-way valve 404 moves between a closed position (FIG. 4) and an open position (FIG. 5) based on pressure changes within the decontamination chamber 102. For example, the valve 404 could be urged towards the closed position, but move to the open position in response to a pressure drop. This allows decontamination fluid 120 within the container 200 to be released by the valve 404 based on pressure changes during the decontamination cycle. The valve 404 could be configured to selectively dispense the decontamination fluid 120 one or more times during a decontamination cycle based on pressure changes within the decontamination chamber 102. The valve 404 prevents any unused sterilant from escaping the container 200 when the cycle is finished. This protects the user from the unused sterilant when collecting the sterilant pod 400.

At ambient pressure, which is shown in FIG. 4, the valve 404 is in the closed position and prevents the decontamination fluid 120 in the container 200 from being released. During a pressure drop in a decontamination cycle, which is shown in FIG. 5, the pressure difference between the inside and outside of the sterilant pod 400 causes the valve 404 to move to the open position, which allows decontamination fluid 120 to be released. The pressure at which the valve 404 moves between the open position and the closed position could vary depending on the expected pressures within the decontamination chamber 102 during the decontamination cycles. In some embodiments, the valve 404 could move to the open position when the pressure in the decontamination chamber 102 is less than 10 Torr.

EXAMPLES

Illustrative examples of the method and system disclosed herein are provided below. An embodiment of the method and system may include any one or more, and any combination of, the examples described below.

Example 1 is a decontamination system. The decontamination system comprises a decontamination chamber, a pump, and a sealed container. The decontamination chamber defines a device receiving area dimensioned to receive a device to be decontaminated. The pump is configured to reduce pressure within the device receiving area. The sealed container defines a cavity with a decontamination fluid. The sealed container is configured to release the decontamination fluid into the device receiving area responsive to a pressure drop applied to the sealed container.

In Example 2, the subject matter of Example 1 is further configured such that the sealed container is configured to release decontamination fluid upon reaching a predetermined pressure drop within the device receiving area.

In Example 3, the subject matter of Example 2 is further configured such that the sealed container is sealed with a membrane seal.

In Example 4, the subject matter of Example 3 is further configured such that the membrane seal is configured to burst upon reaching the predetermined pressure drop in the device receiving area, thereby releasing the decontamination fluid.

In Example 5, the subject matter of Example 1 is further configured such that the sealed container includes a one-way valve in fluid communication with the cavity configured to allow flow out of the cavity, but prevent flow into the cavity.

In Example 6, the subject matter of Example 5 is further configured such that the one-way valve is configured to open upon reaching a predetermined pressure drop in the device receiving area, thereby releasing the decontamination fluid.

In Example 7, the subject matter of Example 1 is further configured such that the decontamination fluid is configured to be stored as a sterilant liquid when stored in the sealed container.

In Example 8, the subject matter of Example 7 is further configured such that the sterilant liquid is configured to be released as a sterilant vapor upon opening the sealed container.

Example 9 is a sterilant pod for a decontamination system. The sterilant pod comprises a sealed container defining a cavity. A decontamination fluid is stored in the cavity. The sealed container is configured to release the decontamination fluid responsive to a predetermined pressure drop proximate the sealed container.

In Example 10, the subject matter of Example 9 is further configured such that the sealed container is sealed with a membrane seal.

In Example 11, the subject matter of Example 10 is further configured such that the membrane seal is configured to burst upon reaching the predetermined pressure drop proximate the sealed container, thereby releasing the decontamination fluid.

In Example 12, the subject matter of Example 9 is further configured such that the sealed container includes a one-way valve in fluid communication with the cavity. In this example, the one-way valve is configured to allow flow out of the cavity, but prevent flow into the cavity.

In Example 13, the subject matter of Example 12 is further configured such that the one-way valve is configured to open upon reaching a predetermined pressure drop proximate the sealed container, thereby releasing the decontamination fluid.

In Example 14, the subject matter of Example 13 is further configured such that the one-way valve is integral with the sealed container.

In Example 15, the subject matter of Example 9 is further configured such that the decontamination fluid is configured to be stored as a sterilant liquid when stored in the sealed container.

In Example 16, the subject matter of Example 15 is further configured such that the sterilant liquid is configured to be released as a sterilant vapor upon opening the sealed container.

Example 17 is a method of decontaminating a device. The method includes the step of providing a decontamination system with a device receiving area. A sealed container with a decontamination fluid is placed into the device receiving area. The decontamination fluid is released from the sealed container by generating a pressure drop in the device receiving area.

In Example 18, the subject matter of Example 17 is further configured such that the releasing step includes bursting a membrane seal due to the pressure drop in the device receiving area.

In Example 19, the subject matter of Example 18 is further configured such that the releasing step includes opening a one-way valve integral with the sealed container due to the pressure drop in the device receiving area.

In Example 20, the subject matter of Example 17 is further configured such that the releasing step vaporizes a liquid sterilant stored in the sealed container.

Although the present disclosure has been described with reference to particular means, materials and embodiments, from the foregoing description, one skilled in the art can easily ascertain the essential characteristics of the invention and various changes and modifications may be made to adapt the various uses and characteristics without departing from the spirit and scope of the invention.

What is claimed is:

1. A decontamination system comprising:
   a decontamination chamber defining a device receiving area dimensioned to receive a device to be decontaminated;
   a lumen device container located within the device receiving area;
   a pump configured to reduce pressure within the device receiving area; and
   a sealed container defining a cavity with a decontamination fluid located in the decontamination chamber and outside of the lumen device container;
   wherein the sealed container is configured to release the decontamination fluid into the lumen device container responsive to a pressure drop applied to the sealed container.

2. The decontamination system of claim 1, wherein the sealed container is configured to release decontamination fluid upon reaching a predetermined pressure drop within the device receiving area.

3. The decontamination system of claim 2, wherein the sealed container is sealed with a membrane seal.

4. The decontamination system of claim 3, wherein the membrane seal is configured to burst upon reaching the predetermined pressure drop in the device receiving area, thereby releasing the decontamination fluid into the lumen device container.

5. The decontamination system of claim 1, wherein the sealed container includes a one-way valve in fluid communication with the cavity, wherein the one-way valve is configured to allow flow out of the cavity, but prevent flow into the cavity.

6. The decontamination system of claim 5, wherein the one-way valve is configured to open upon reaching a predetermined pressure drop in the decontamination chamber, thereby releasing the decontamination fluid.

7. The decontamination system of claim 1, wherein the decontamination fluid is configured to be stored as a sterilant liquid when stored in the sealed container.

8. The decontamination system of claim 7, wherein the sterilant liquid is configured to be released as a sterilant vapor upon opening the sealed container.

9. A sterilant pod for a decontamination system, the sterilant pod consisting of:
   a sealed container defining a cavity; and
   a decontamination fluid stored in the cavity;
   wherein the sealed container is configured to prevent the decontamination fluid from escaping the container at ambient pressure and to release the decontamination fluid responsive to a predetermined pressure drop proximate the sealed container.

10. The sterilant pod of claim 9, wherein the sealed container is sealed with a membrane seal.

11. The sterilant pod of claim 10, wherein the membrane seal is configured to burst upon reaching the predetermined pressure drop proximate the sealed container, thereby releasing the decontamination fluid.

12. The sterilant pod of claim 9, wherein the sealed container includes a one-way valve in fluid communication with the cavity, wherein the one-way valve is configured to allow flow out of the cavity, but prevent flow into the cavity.

13. The sterilant pod of claim 12, wherein the one-way valve is configured to open upon reaching a predetermined pressure drop proximate the sealed container, thereby releasing the decontamination fluid.

14. The sterilant pod of claim 13, wherein the one-way valve is integral with the sealed container.

15. The sterilant pod of claim 9, wherein the decontamination fluid is configured to be stored as a sterilant liquid when stored in the sealed container.

16. The sterilant pod of claim 15, wherein the sterilant liquid is configured to be released as a sterilant vapor upon opening the sealed container.

17. A method of decontaminating a device, the method comprising the steps of:
- providing a decontamination system with a device receiving area and a lumen device container located within the device receiving area;
- placing a sealed container with a decontamination fluid into the device receiving area outside of the lumen device container; and
- releasing the decontamination fluid from the sealed container into the lumen device container by generating a pressure drop in the device receiving area.

18. The method of claim 17, wherein the releasing step includes bursting a membrane seal due to the pressure drop in the device receiving area.

19. The method of claim 18, wherein the releasing step includes opening a one-way valve integral with the sealed container due to the pressure drop in the device receiving area.

20. The method of claim 17, wherein the releasing step vaporizes a liquid sterilant stored in the sealed container.

* * * * *